United States Patent [19]

Redus

[11] Patent Number: 5,031,465

[45] Date of Patent: Jul. 16, 1991

[54] STEAM QUALITY AND MASS FLOW RATE MEASUREMENT USING CRITICAL FLOW CHOKE UPSTREAM OF AN ORIFICE PLATE

[75] Inventor: Clifford L. Redus, Katy, Tex.

[73] Assignee: Texaco Inc., White Plains, N.Y.

[21] Appl. No.: 529,819

[22] Filed: May 29, 1990

[51] Int. Cl.⁵ .............................................. G01F 1/74
[52] U.S. Cl. .................................. 73/861.04; 73/29.03
[58] Field of Search ................. 73/29.01, 29.03, 861.04

[56] References Cited

U.S. PATENT DOCUMENTS 4,836,032  6/1989  Redus et al. ..................... 73/861.04

Primary Examiner—Herbert Goldstein
Attorney, Agent, or Firm—Jack H. Park; Kenneth R. Priem; Russell J. Egan

[57] ABSTRACT

A method and apparatus for measuring steam quality and mass flow rate at an injection wellhead includes measuring upstream pressure before a critical flow choke, downstream pressure after the choke and differential pressure across an orifice plate spaced downstream of the choke.

6 Claims, 1 Drawing Sheet

STEAM QUALITY AND MASS FLOW RATE MEASUREMENT USING CRITICAL FLOW CHOKE UPSTREAM OF AN ORIFICE PLATE

BACKGROUND OF THE INVENTION

1. The Field of the Invention

This invention concerns a method for measuring the quality of a saturated steam flow. In particular, it relates to a method and apparatus for determining the quality of wet steam used for enhanced recovery of petroleum products from a reservoir, which steam has relatively low quality due to the presence of water with the steam's vaporous component.

2. The Prior Art

Steam flooding has become an accepted practice for secondary recovery of petroleum products from marginal fields or heavy oil reservoirs that require a degree of stimulation to produce a satisfactory flow of crude petroleum. There is a need for a simple method and apparatus to determine the quality of saturated steam at the wellhead of an injection well sending steam to such reservoirs. Such a measurement, if simplified, would be particularly useful in determining the amount of heat which is applied to the underground reservoir by the injected steam.

The measurement or monitoring of steam quality is important since the steam's quality, and thereby its reservoir or formation heatup effect, directly affects the resulting production operations. Further, the quality of the steam which can be most economically injected into a particular substrate or reservoir is contingent on a number of circumstances. The latter include the depth of the reservoir and the anticipated prospects for extracting commercially justified amounts of hydrocarbon products therefrom.

In brief, it is desirable that the quality of steam, that is the mass of the steam vapor divided by the total mass, and the mass flow rate, which is injected into each injection well be altered or adjusted to a level of quality that best conforms to the condition of the formation penetrated by that well. Clearly the quality of the steam and the mass flow rate must be known before any alteration or adjustment can be made.

It is known that in order to be particularly effective in this type of enhanced oil recovery operation (EOR), the flow of injected steam must be monitored by use of metering means positioned in the steam-carrying line adjacent the wellhead. It can be appreciated that steam will normally leave the steam generator or source at a known quality, pressure and mass flow rate. As the pressurized steam flow progresses towards an injection well, however, the quality will usually be substantially decreased. A decrease in the quality can be based on such factors as the distance between the well and the source, the effectiveness of the pipe insulation and weather conditions including ambient temperature and wind velocity. It will further depend on the pipe layout including number and orientation of pipe Tees through which the steam has to travel prior to reaching the injection port or well because of phase separation that can occur in these pipe Tees.

It is important, therefore, as a matter of economic practicality that a flow monitoring and controlling means be instituted into the steam pipeline immediately upstream of each injection wellhead. In many steamflood operations, a choke mechanism is placed in the steam line to constrict the steam flow to thereby allow regulation of the mass flow rate of the steam which enters that particular well.

In my prior U.S. Pat. No. 4,836,032, I disclosed the use of an orifice plate in series with a critical flow choke to provide a method of measurement for both steam quality and mass flow rate. Either the orifice plate or the choke alone can be used to measure steam quality and mass flow rate. However, a mathematical expression for steam quality through both devices is obtained by solving an independent mass flow rate equation for each device, an equation for wet steam through the critical flow choke and an equation for wet steam through a sharp-edged orifice plate. The present invention is distinguished from my earlier invention by the fact that the earlier invention requires two measurements, namely pressure at the entrance to the flow choke and the differential pressure across the orifice plate. The calculation procedure of the present invention uses three measurements: (1) upstream pressure before the choke; (2) downstream pressure after the choke; and (3) a differential pressure across the orifice plate. Application of a critical flow choke before the orifice plate requires a constant enthalpy quality change relationship because of the large pressure drop through the choke (between measurement points 1 and 2 above) to achieve a critical flow.

BRIEF SUMMARY OF THE INVENTION

The present invention concerns a method and apparatus for measuring steam quality (mass of steam vapor divided by the total mass of water and steam vapor) of wet saturated steam. The invention comprises, in brief, a method and apparatus to determine the quality of product stimulation wet steam which is to be injected into a well for producing hydrocarbon products from a heavy reservoir being steamflooded for secondary oil recovery. The method is based on the determination of certain characteristics of steam at the injection wellhead. Knowing these characteristics will permit the desired quality determination to be made and, therefore, appropriate adjustments of the steam quality for efficient oil recovery. More precisely, the method and apparatus of the present invention are addressed to measuring steam quality and mass flow rate in a steam line to a desired degree prior to injection of the steam flow into a hydrocarbon-containing substrate by means of an injection well.

Stated in another way, in any process involving steam injection for a secondary oil recovery procedure, a persistent problem exists in making a rapid and accurate determination of the quality and mass flow rate of steam being injected into an individual well or a group of wells. Such knowledge is relevant to production efficiency because the steam quality and mass flow rate directly affect the production operation at the production well and, consequently, the investment requirements for similar steam flooding projects.

It is known to be desirable, and highly practical from an economic consideration, to mix saturated water with a high quality steam for achieving a lower but adequate quality steam at each specific wellhead. In such an instance the present invention provides for a means and method to quickly and accurately determine the quality of the steam and its mass flow rate.

It has been determined, for instance, that the approximately 20.000 barrels of oil a day must be burned to generate sufficient high-quality wet steam for the production of hydrocarbons in a typical secondary oil recovery from a field. The cost efficiency of this type of steam flood operation can be improved noticeably by economizing the distribution of the steam. This economizing requires an accurate measurement of steam quality and mass flow rate.

Steam quality tapering, and conversion to hot water floods at various field well patterns, have mandated the accurate measurement of steam quality and mass flow rates at individual injection wells. Also, the phenomena of two-phase flow in conduits, as well as phase splitting, have caused steam qualities and mass rates at injection wells to be greater or less than the desired qualities necessary for effective reservoir management.

It is therefore an object of the present invention to provide a method and apparatus for determining the quality of steam which is injected into a steam injection wellhead. Once the wellhead steam quality has been determined with the device, conventional heat loss or pressure drop conditions can be used to determine reservoir sand face conditions.

It is a further object to provide a method and apparatus for readily determining the quality and mass flow rate of wet steam being injected through a wellhead and into a hydrocarbon producing reservoir whereby the hydrocarbon production efficiency is improved.

It is a still further object to provide means for measuring the quality and adjusting the flow rate of steam, under critical flow, which is injected into a hydrocarbon-producing substrate by way of a critical flow choke which regulates steam flow entering the injection well, given a measured steam quality.

BRIEF DESCRIPTION OF THE DRAWINGS

The present invention will now be described, by way of example, with reference to the accompanying drawings in which.

DETAILED DESCRIPTION OF THE PREFERRED EMBODIMENT

Figure 1:
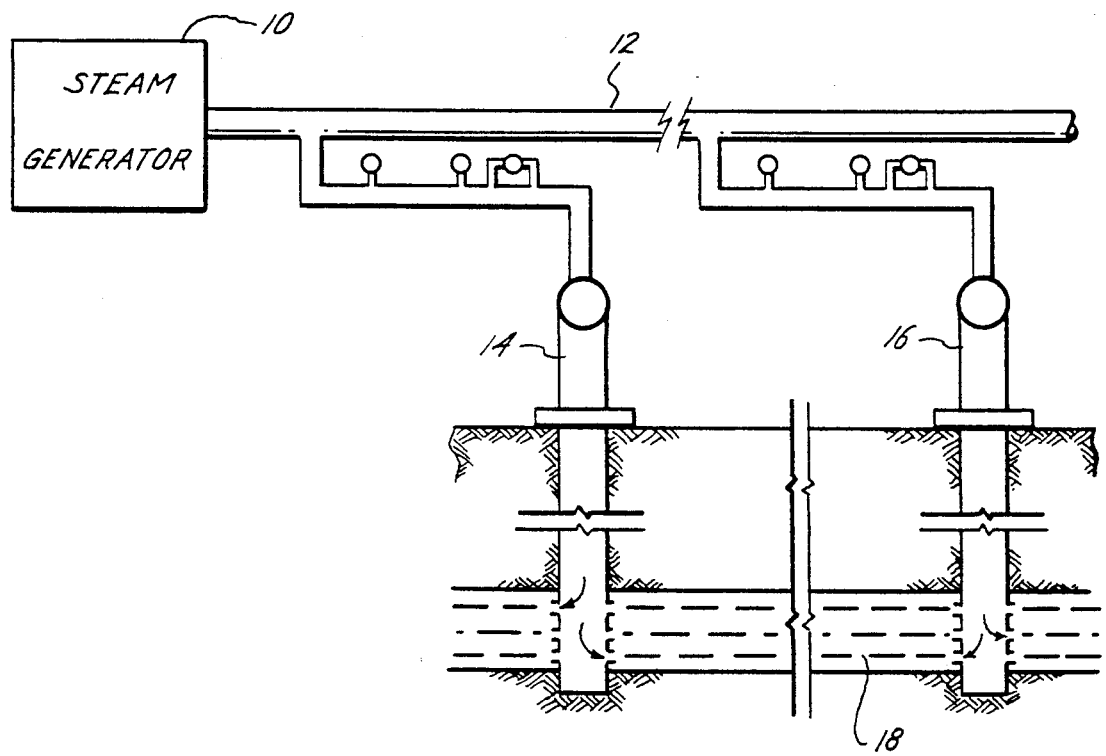
FIG. 1 is a schematic representation of the present invention incorporated into a steam line distribution system in a typical steam flood, secondary recovery operation.

The present invention, with reference to FIG. 1, relates to a method and apparatus for determining the quality and mass flow rate of a steam flow. This determination is usually made immediately prior to the steam being injected into a hydrocarbon containing reservoir. The steam is produced by generator 10 and fed by a series of conduits 12 to individual injection wellheads 14, 16 for injection into a substrate 18. It is readily appreciated that the steam coming from the generator 10 will deteriorate in quality as it passes through the conduits 12, particularly as the steam loses heat and when the steam encounters a pipe Tee which splits the steam into multiple lines. As the steam travels through the conduits 12, there is the general tendency to form an annular flow with the liquid phase being adjacent to the walls of the conduit and the gaseous phase following generally axially along the conduit. This flow pattern will be disrupted by almost every encounter with a joint or fitting of the conduit, particularly pipe Tees. The mixture of the liquid and vapor phases thus is largely determined by the distance traveled between generator and wellhead, the insulation on the conduit, the weather conditions including ambient temperature and wind velocity and the path or route taken by this steam insofar as splitting will cause a quality change to occur.

Figure 2:
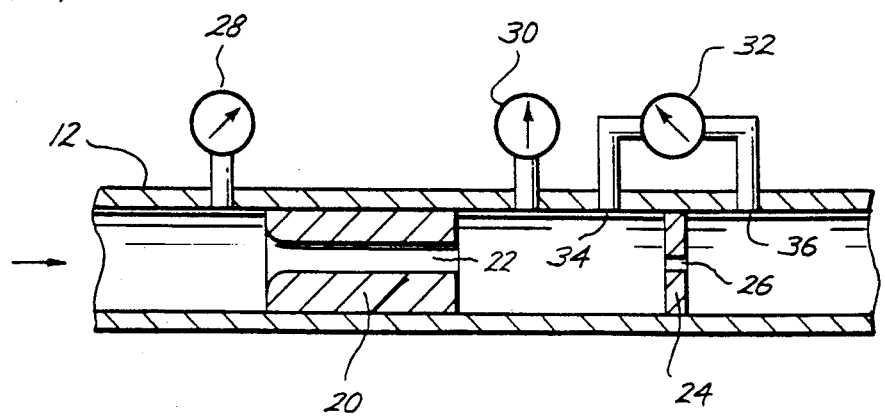
FIG. 2 is a schematic section through a single steam quality measuring apparatus according to the present invention.

Referring to FIG. 2, the conduit 12 is furnished with a choke 20 having a central flow passage or bean 22 of sufficient diameter t constrict the pressurized steam to assure or provide critical flow. The apparatus further includes a sharp-edge orifice plate 24 which is fastened transversely across the conduit 12 and spaced downstream of the choke 20. The aperture 26 of this plate 24 is coaxial with the conduit 12 and aligned with bean 22. Steam pressure meters 28, 30 are located in the conduit on either end of the choke 20 and the differential pressure-reading meter 32 is positioned in the conduit with openings 34, 36 on opposite sides of the orifice plate 24.

The combination of the orifice plate 24 and choke 20 are employed for measuring steam quality and the mass flow rate at injection wellheads with the critical flow choke utilized primarily to control the steam injection rate.

Referring back to FIG. 1, the normally insulated steam flow pipeline on conduit 12 includes fittings, couplings, flanges and the like (all of which are known and none of which have been shown for sake of simplicity of the drawing) into which a flow of steam is directed from a pressurized source, namely the generator 10, to the wellheads. Steam at the injection well typically has a quality between 10 and 80 percent, a mass flow rate from 100 to 400 barrels of steam per day cold water equivalent (BSPD-CWE) and a pressure between 300 and 700 psig. Even though empirical correction was tested over these operating conditions, the device will work over flow rate ranges from 50 to 5000 BSPD-CWE and pressures from 100 to 2000 psig with appropriate modification of the empirical constants. The function of the choke in this type of steam injection operation is to constrict the flow of steam passing therethrough to a reduced diameter to thereby cause the flow at the choke downstream from the discharge side to be critical. Operationally, as the steam issues from the high pressure source, it will be of a known quality, depending primarily upon its water content. For example, the greater percentage of saturated water intermixed with the steam vapor phase, the lesser will be the quality of the saturated steam. Since the steam quality will be subject to reduction in any conduit that carries the hot flow, the conduit is provided with suitable insulation or cover to minimize heat loss through the conduit's metallic walls.

As noted herein, the use of a critical flow choke and orifice plate provides rapid and accurate method for measurement of both steam quality and mass flow rate. Neither the orifice plate nor choke alone is capable of providing a measurement to determine steam quality. However, the expression or empirical formula for steam quality through both of these devices is obtained by solving an independent mass flow rate equation for each device.

In steam injection networks, a pressing concern is steam quality and rate at various points in the distribution network. A method and apparatus for determining this steam quality is the subject of the present invention. In order to determine the steam quality and rate in a wet steam line, two independent measurements must be made. In the subject invention, they are a critical flow choke 20 in series with an orifice plate 24. The critical flow through the choke can be expressed by the Thornhill-Craver equation as:

$$W = 61.10C^2 C_c \sqrt{\frac{P_1}{X_1 U_{fg1} + U_{f1}}} \quad (1)$$

where
$P_2/P_1 < 0.52$ where $C_c = 1 - 0.00705 L/C$ (2)

The James equation can be used to describe the flow through the orifice plate as:

$$W = \frac{24.65 C_o d^2 Y}{\sqrt{1-\beta^4}} \sqrt{\frac{\phi}{X_2^{1.5} U_{fg2} + U_{f2}}} \quad (3)$$

where $$Y = \sqrt{r \frac{2}{\gamma}\left(\frac{\gamma}{\gamma-1}\right)\left(\frac{1 - r^{\frac{\gamma-1}{\gamma}}}{1-r}\right)\left(\frac{1-\beta^4}{1-\beta^4 r^{\frac{2}{\gamma}}}\right)} \quad (4)$$

where
$\gamma = 1.3$ and $$r = 1 - \frac{\phi}{27.692 P_2}. \quad (5)$$

Relationship between $X_1$ and $X_2$

Assuming no heat transfer between points 1 and 2, the steam enthalpies must be equal i.e., $h = h_1 = h_2.$ (6)

Equation (6) becomes
$h_{f1} + X_1 h_{fg1} = h_{f2} + X_2 h_{fg2}.$ (7)

which can be solved for $X_1$ as $$X_1 = X_2 \left(\frac{h_{fg2}}{h_{fg1}}\right) + \frac{h_{f2} - h_{f1}}{h_{fg1}}. \quad (8)$$

Conservation of Mass

The conservation of mass through the device can be expressed as $\eta(X_2) = W_{choke} - W_{orifice} = 0.$ (9)

where $\eta$ is derived from equations (1), (3) and (8) as $\eta(X_2) =$ (10)

$$61.10 c^2 C_c \sqrt{\frac{P_1}{U_{f1} + U_{fg1}\left[X_2\left(\frac{h_{fg2}}{h_{fg1}}\right) + \frac{h_{f2} - h_{f1}}{h_{fg1}}\right]}} -$$

$$\frac{24.65 C_o d^2 Y}{\sqrt{1-\beta^4}} \sqrt{\frac{\phi}{X_2^{1.5} U_{fg2} + U_{f2}}}$$

Equation (10) can be solved iteratively using the secant method (letting $X = X_2$)

$$X^{(i+1)} = X^{(i)} - \frac{\eta(X^{(i)})[X^{(i)} - X^{(i-1)}]}{[\eta(X^{(i)}) - \eta(X^{(i-1)})]}, \quad (11)$$

where first and second iterates are $X^{(1)} = 0.8,$ (12)

and $X^{(2)} = 0.7.$ (13)
Convergence is obtained when
$|X^{(i-1)} - X^{(i)}| < \epsilon$ (14)

where
$\epsilon = 0.0001$ (15)

Then $X_2 = X_i$ where i=converged iterate index. The steam quality $X_i$ is then calculated from equation (8) and the steam mass flow rate W is calculated from equation (1).

Specific volume and enthalphy for steam vapor and liquid can be obtained from the Keenan & Keyes steam tables by empirical equations that approximate the values.

Sample Calculation
Given:
$P_1 = 500$ psia
$P_2 = 250$ psia
$c = 0.4$ in
$L = 6$ in
$\beta = 0.7$
$D = 2$ in
$C_o = 0.61$
$d = \beta D = 1.4$ in
$C_c = 0.9788$ from equation (2)
$\phi = 67.29$ in of water
Find: $W_1$, $X_1$, $X_2$
Solution:
From Steam Tables:
$\theta_{g1} = 0.9283$ ft³/lbm, $\theta_{g2} = 1.8448$ ft/lbm,
$\theta_{f1} = 0.019748$ ft³/lbm, $\theta_{f2} = 0.018653$ ft³/lbm,
$\theta_{fg1} = 0.90855$ ft³/lbm, $\theta_{fg2} = 1.82615$ ft³/lbm
and,
$h_{f1} = 449.5$ Btu/lbm, $h_{f2} = 376.2$ Btu/lbm,
$h_{fg1} = 755.8$ Btu/lbm, $h_{fg2} = 825.8$ Btu/lbm.
Check for Critical Flow Across Choke $$\frac{P_2}{P_1} = \frac{250}{200} \; 0.5 < 0.52 \therefore \text{Critical Flow}$$

Assume $Y \approx 1$ $$\eta(X_2) = 61.10(0.4)^2(0.9788) \sqrt{\cfrac{500}{.019748 + .90855\left[X_2\left(\cfrac{825.8}{755.8}\right) + \cfrac{(376.2 - 449.5)}{755.8}\right]}} -$$

$$\cfrac{24.65(0.61)(1.4)^2(1)}{\sqrt{1 - 0.7^4}} \sqrt{\cfrac{67.29}{X_2^{1.5} 1.82615 + 0.018653}}$$

simplifying $$\eta(X_2) = \cfrac{213.964}{\sqrt{.99270X_2 - 0.06837}} - \cfrac{277.332}{\sqrt{X_2^{1.5} 1.82615 + 0.018653}}$$

| Iteration | i | $X_2(i)$ | $\eta(X_2^{(i)})$ |
|---|---|---|---|
| | 1 | 0.80 | 10.251 |
| | 2 | 0.70 | 4.457 |
| | 3 | 0.623 | −1.181 |
| | 4 | 0.639 | 0.091 |
| $X_2 =$ | 5 | 0.6379 | |

$$X_1 = X_2\left(\cfrac{h_{fg2}}{h_{fg1}}\right) + \cfrac{h_{f2} - h_{f1}}{h_{fg1}} =$$

$$0.6379\left(\cfrac{825.8}{755.8}\right) + \cfrac{376.2 - 499.5}{755.8}$$

$X_1 = 0.600$ $$W = 61.1c^2 C_c \sqrt{\cfrac{P_1}{X_1 U_{fg1} + U_{f1}}} =$$

$$61.1(.4)^2(.9788)\sqrt{\cfrac{500}{(.6)(.90855) + .019748}}$$

W = 284.68 BSPD-CWE
W = Mass flow rate BWPD-CWE
$C_o$ = Discharge coefficient of orifice plate
$C_c$ = Discharge coefficient of choke
d = Orifice diameter, inches
D = Inner diameter of the pipe, inches
c = Choke diameter, inches
E = Convergence tolerance
Y = Orifice plate expansion factor
φ = Orifice plate differential head — (inches of water)
β = d/D
$X_1$ = Steam quality at point (1), fraction
$X_2$ = Steam quality at point (2), fraction
$0_{gi}$ = Specific volume of steam vapor at Pressure Pi (ft³/lbm)
$0_{fgi}$ = Specific volume of water at Pressure Pi (ft³/lbm)
$0_{fi} = 0_{gi} - 0_{fi}$ at Pressure Pi where i = 1 or 2
L = Bean or chore body length, inches
$P_1$ = Absolute pressure at point 1, psia
$P_2$ = Absolute pressure at point 2, psia The present invention may be subject to changes and modification without departing from the spirit or essential characteristics of the invention. The above description should therefor be considered in all respects as being illustrative and not restrictive of the invention as defined in the following claims.

What is claimed is:

1. An apparatus for determining the mass flow rate and quality of pressurized steam flowing through a conduit which apparatus comprises:

a choke member in said conduit having a flow passage of a diameter to constrict the flow of steam in the conduit to a critical flow;

an orifice plate in said conduit positioned downstream of said choke member to define an intermediate passage therebetween and having an orifice axially aligned with the flow passage of said choke member;

means for measuring the pressure differential across said orifice plate;

means for measuring the steam pressure in said intermediate passage;

means for measuring the steam pressure upstream of said choke member; and means for determining the mass flow rate and quality of steam in aid conduit in accordance with said pressure differential across the orifice and the pressure upstream of the choke member, the pressure in said intermediate passage being used to calculate water and steam vapor specific volume upstream of said orifice plate.

2. An apparatus as defined in claim 1 wherein the critical flow through the choke is defined by $$W = 61.10c^2 C_c \sqrt{\cfrac{P_1}{X_1 U_{fg1} + U_{f1}}}.$$

where $P_2/P_1 < 0.52$ and $C_c = 1 - 0.00705$ L/c wherein
W = Mass flow rate (BWPD-CWE)
$C_c$ = Discharge coefficient of choke
c = Choke diameter (inches)
$P_1$ = Absolute pressure before the choke (psia)
$P_2$ = Absolute pressure after the choke (psia)
$X_1$ = Steam quality before the choke (fraction)
$X_2$ = Steam quality after the choke (fraction)
$0_{fi}$ = Specific volume of water before the choke (ft³/lbm)
$0_{gl}$ = Specific volume of steam vapor before the choke (ft³/lbm)
$0_{fgl} = 0_{gl} - 0_{fl}$ (ft³/lbm)
L = Bean or choke body length (inches)

3. An apparatus as defined in claim 1 wherein the flow through the orifice plate is defined by $$W = \cfrac{24.65 C_o d^2 Y}{\sqrt{1 - \beta^4}} \sqrt{\cfrac{\phi}{X_2^{1.5} U_{fg2} - U_{f2}}}$$

where $$Y = \sqrt{r^{\frac{2}{\gamma}}\left(\frac{\gamma}{\gamma-1}\right)\left(\frac{1-r^{\frac{\gamma-1}{\gamma}}}{1-r}\right)\left(\frac{1-\beta^4}{1-\beta^4 r^{\frac{2}{\gamma}}}\right)}$$

where $\gamma = 1.3$ and $$r = 1 - \frac{\phi}{27.692 P_2}$$

wherein:
W = Mass flow rate (BWPD-CWE)
$C_o$ = Discharge coefficient of the orifice plate
d = Orifice diameter (inches)
Y = Orifice plate expansion factor
$\phi$ = Orifice plate differential head (inches of water)
$\beta = d/D$
D = Inner diameter of pipe (inches)
$X_2$ = Steam quality before plate (fraction)
$0_{f2}$ = Specific volume of water before plate (ft$^3$/lbm)
$0_{fg2} = 0_{g2} - 0_{f2}$
$0_{g2}$ = Specific volume of steam vapor before plate (ft$^3$/lbm)

4. A method for determining the mass flow rate and quality of pressurized steam flowing through a conduit which method comprises:
  constricting the flow of steam in a conduit to a critical flow by means of a choke member;
  defining an intermediate passage between said choke member and an orifice plate spaced downstream from said choke member with the aperture of said orifice plate aligned with the flow passage of said choke member;
  measuring the pressure differential across said orifice plate;
  measuring the steam pressure in said intermediate passage;
  measuring the steam pressure upstream of said choke member; and
  determining the mass flow rate and the quality of steam in said conduit in accordance with said pressure differential across the orifice and the pressure upstream of the choke member, the intermediate passage pressure being used to calculate water and steam vapor specific volume upstream of the orifice plate.

5. The method as defined in claim 4 wherein the critical flow through the choke is defined by $$W = 61.10 c^2 C_c \sqrt{\frac{P_1}{X_1 U_{fg1} + U_{f1}}}$$

where $P_2/P_1 < 0.52$ and $C_c = 1 - 0.00705$ L/c wherein
W = Mass flow rate (BWPD-CWE)
$C_c$ = Discharge coefficient of the choke
c = Choke diameter (inches)
$P_1$ = Absolute pressure before the choke (psia)
$P_2$ = Absolute pressure after the choke (psia)
$X_1$ = Steam quality before the choke (fraction)
$0_{f1}$ = Specific volume of water before the choke (ft$^3$/lbm)
$0_{g1}$ = Specific volume of steam vapor before the choke (ft$^3$/lbm)
$0_{fg1} = 0_{g1} - 0_{f1}$ (ft$^3$/lbm)
L = Bean or choke body Length (inches)

6. The method as defined in claim 4 wherein the flow through the orifice plate is defined by $$W = \frac{24.65 C_o d^2 Y}{\sqrt{1-\beta^4}} \sqrt{\frac{\phi}{X_2^{1.5} U_{fg2} + U_{f2}}}$$

where $$Y = \sqrt{r^{\frac{2}{\gamma}}\left(\frac{\gamma}{\gamma-1}\right)\left(\frac{1-r^{\frac{\gamma-1}{\gamma}}}{1-r}\right)\left(\frac{1-\beta^4}{1-\beta^4 r^{\frac{2}{\gamma}}}\right)}. \quad (4)$$

where $\gamma = 1.3$ and $$r = 1 - \frac{\phi}{27.692 P_2}$$

wherein
W = Mass flow rate (BWPD-CWE)
$C_o$ = Discharge coefficient of the orifice plate
d = Orifice diameter (inches)
Y = Orifice plate expansion factor
$\phi$ = Orifice plate differential head, (inches of water)
$\beta = d/D$
D = Inner diameter of pipe (inches)
$X_2$ = Steam quality before the plate (fraction)
$0_{f2}$ = Specific volume of water before the plate (ft$_3$/lbm)
$0_{fg2} = 0_{g2} - 0_{f2}$ (ft$^3$/lbm)
$0_{g2}$ = Specific volume of steam vapor before the plate (ft$^3$/lbm).

* * * * *

UNITED STATES PATENT AND TRADEMARK OFFICE
CERTIFICATE OF CORRECTION

PATENT NO. : 5,031,465

DATED : July 16, 1991

INVENTOR(S) : Clifford L. Redus

It is certified that error appears in the above-identified patent and that said Letters Patent is hereby corrected as shown below:

Column 5, Lines 7 and 21 in the equation change "U" (both occurrences) to the Greek theta --$\theta$--

Column 6, Lines 5, 11 and 55 in the equation change "U" (each occurrence) to the Greek theta --$\theta$--

Column 7, Line 38 in the equation change "U" to the Greek theta --$\theta$--

Col. 8;
Claim 2, Line 3 in the equation change "U" to the Greek theta --$\theta$--

Col. 8;
Claim 3, Line 3 in the equation change "U" to the Greek theta --$\theta$--

Col. 10;
Claim 5, Line 3 in the equation change "U" to the Greek theta --$\theta$--

Column 6, Lines 56, 57 and 58 in the equation change the "O" (each occurrence) to the Greek theta --$\theta$--

Column 7, Lines 57, 59 and 61 in the equation change the "O" (each occurrence) to the Greek theta --$\theta$--

Column 8, Lines 12, 13 and 14 in the equation change the "O" (each occurrence) to the Greek theta --$\theta$--

UNITED STATES PATENT AND TRADEMARK OFFICE
CERTIFICATE OF CORRECTION

PATENT NO. : 5,031,465

DATED : July 16, 1991

INVENTOR(S) : Clifford L. Redus

It is certified that error appears in the above-identified patent and that said Letters Patent is hereby corrected as shown below:

Col. 8;

Claim 3, Lines 17, 18 and 19 in the equation change the "O" (each occurrence) to the Greek theta --$\theta$--

Col. 10;

Claim 5, Lines 11, 13 and 14 in the equation change the "O" (each occurrence) to the Greek theta --$\theta$--

Col. 10;

Claim 6, Lines 17, 19 and 20 in the equation change the "O" (each occurrence) to the Greek theta --$\theta$--

Col. 8, Claim 1, Line 18 after "and" insert "the"

Signed and Sealed this

Nineteenth Day of October, 1993

*Attest:*

BRUCE LEHMAN

*Attesting Officer*

*Commissioner of Patents and Trademarks*